(12) United States Patent
Fabunan

(10) Patent No.: US 6,172,053 B1
(45) Date of Patent: Jan. 9, 2001

(54) INJECTION VIRAL TREATMENT

(76) Inventor: Ruben G. Fabunan, 329 N. Vendome St., Los Angeles, CA (US) 90026

( * ) Notice: Under 35 U.S.C. 154(b), the term of this patent shall be extended for 0 days.

(21) Appl. No.: 09/395,290

(22) Filed: Sep. 13, 1999

Related U.S. Application Data

(60) Provisional application No. 60/121,479, filed on Feb. 24, 1999.

(51) Int. Cl.⁷ .................................................. A61K 31/56
(52) U.S. Cl. ........................................... 514/171; 514/934
(58) Field of Search ...................... 514/171, 934

(56) References Cited

U.S. PATENT DOCUMENTS

| | | |
|---|---|---|
| 4,478,822 | 10/1984 | Haslam . |
| 5,492,901 | 2/1996 | Fahunan . |
| 5,510,339 | 4/1996 | Gleich . |
| 5,837,729 | 11/1998 | Bourinhaiar . |
| 5,922,340 | 7/1999 | Berde . |

OTHER PUBLICATIONS

Bhargava et al., "Jaipur block in postherpetic neuralgia." International Journal of Dermatology, vol. 37(6), pp. 465–468, 1998.*

* cited by examiner

*Primary Examiner*—Barbara Badio
(74) *Attorney, Agent, or Firm*—Barbara R. Greenberg

(57) ABSTRACT

The present invention relates to a therapeutic composition and formulation for the treatment of viral diseases such as, Dengue fever and influenza. More particularly, to therapeutic preparation comprising substantially water soluble, local anesthetic of the ester type, procaine hydrochloride and a water soluble glucocorticoid, dexamethasone sodium phosphate.

8 Claims, No Drawings

INJECTION VIRAL TREATMENT

This application is a NON-provisional application filed under U.S.C. §111(a) within 12 months of Provisional application Ser. No. 60/121,479. This application is a continuation in part of Provisional application Ser. No. 60/121,479 filed on Feb. 24, 1999 and still pending.

FIELD OF THE INVENTION

The present invention relates to a therapeutic composition for the treatment of viral infections and a method of administration thereof. More particularly, the invention relates to a therapeutic composition including a substantially water soluble local anesthetic of the ester type injectable and a water soluble glucocorticoid injectable, and to the method of administering said composition to an infected patient.

BACKGROUND OF THE INVENTION

In both Third-world and developing countries and also in developed countries, there is a prevalent need for an economical yet effective viral treatment to both ease human suffering and save lives. The present invention relates directly to both of these needs since it has been compassionately used to treat and/or cure a number of known pathogenic viruses, including but not limited to human immunodeficiency virus (HIV) causing acquired immunodeficiency syndrome (AIDS), Dengue fever virus, influenza virus, rhinovirus causing common colds, herpes zoster virus, mumps virus, measles virus, hepatitis virus, conjunctivitis virus, rabies virus, chickenpox virus and other viruses found in equatorial environments common to Third-World and developing countries but also found with increasing prevalence in industrialized nations. To the best of the inventor's knowledge, in medical textbooks or in current clinical practice, there is no treatment, cure or vaccine for the Dengue fever virus.

This invention comes about after many years of field testing, and now over two years of clinical studies at the Fabunan Medical Clinic located in the province of Zambales, the Philippines in Southeast Asia. Each known virus that has been treated with this composition has shown a remarkably significant improvement and/or curative result with no serious side effects. Routine cases were clinically diagnosed and then treatment began. A patient usually improved and recovered within seventy two hours but, sometimes, more time was needed.

DESCRIPTION OF THE PRIOR ART

U.S. Pat. No. 5,492,901 issued to Dr. Ruben G. Fabunan, the present inventor, discloses an envenomation antidote for therapeutic use in the treatment of venomous animal bites or stings. The antidote is administered by intramuscular injection and subcutaneous injection along with a slow intravenous injection. The antidote is comprised of procaine hydrochloride with epinephrine and dexamethasone sodium phosphate. The present invention discloses a formulation of procaine hydrochloride without epinephrine and dexamethasone sodium phosphate and is administered only intramuscularly for, surprisingly, the treatment of viral diseases.

U.S. Pat. No. 5,922,340 discloses a glucocorticosteroid used to prolong the duration of a local anesthetic by using a controlled release material.

U.S. Pat. No. 5,837,729 discloses the use of acetaminophen (Tylenol), an analgesic without anti-inflammatory activity, and derivatives thereof, in the treatment and prevention of HIV infections.

U.S. Pat. No. 5,510,339 discloses the use of a topical anesthetic and a glucocorticoid to treat diseases such as bronchial asthma through inhalation therapy.

U.S. Pat. No. 4,478,822 discloses a system for delivering drugs including dexamethasone and procaine directly to a body cavity.

None of the abovementioned prior art citations, taken singly or in combination, appear to describe the present invention as claimed.

SUMMARY OF THE INVENTION

This invention comprises a generic formulation of procaine hydrochloride and dexamethasone sodium phosphate which is injected intramuscularly at certain dosages and regulated dosing intervals. This formulation has its broad spectrum use in treating viral infections, mainly AIDS, Dengue fever and influenza Accordingly, it is a general objective of the present invention to provide a treatment for a broad spectrum of viral diseases which is quickly effective, does not induce serious side effects and can be simply administered in multiple, intramuscular, low volume doses.

Another objective of the present invention is to provide a formulation that can be quickly released for general use since the formulation is comprised of FDA approved generic drugs.

It is still another objective of the present invention to provide a treatment for viral diseases where a patient can experience a short recovery time.

Yet another objective of the present invention is to provide a viral disease treatment that is both easily portable and available in packaged form for immediate use. These and other objectives of the present invention will become readily apparent upon further review of the description of the present invention which follows.

BRIEF DESCRIPTION OF THE DRAWINGS

There are no drawings in this case.

DETAILED DESCRIPTION OF THE INVENTION

The present invention is useful for the effective treatment of viral infections. The viral treatment is prepared from USP approved drugs and has broad application in the treatment of several viral infections, namely AIDS, Dengue fever, influenza, common colds, herpes, mumps, measles, viral hepatitis, conjunctivitis, chickenpox and rabies.

The invention includes a formulation of procaine hydrochloride, USP, combined with dexamethasone sodium phosphate, USP. By itself, procaine hydrochloride is a local anesthetic that blocks the conduction of nerve impulses. It is readily absorbed following parenteral administration and is directly biotransformed in the bloodstream being hydrolyzed by plasma cholinesterase to para-aminobenzoic acid and diethylaminoethanol within one and one half hours from the time of administration. Procaine hydrochloride is the ester of diethylaminoethanol and para-aminobenzoic acid and is related chemically and pharmacologically to ester type local anesthetics. The chemical name of procaine hydrochloride is benzoic acid 4-amino, 2-diethly(amino) ethyl ester monohydrochloride. Dexamethasone sodium phosphate is a water-soluble inorganic ester of dexamethasone. Dexamethasone sodium phosphate, by itself, is used to treat endocrine disorders, rheumatic disorders, collagen diseases, dermatologic diseases, allergic states, ophthalmic diseases, gastrointestinal diseases, respiratory diseases, hematologic disorders, neoplastic diseases and edematous states. Dexamethasone sodium phosphate has the chemical name 9-fluoro-11β,17,21-trihydroxy-16 -methylpregna-1,4-diene-3,20-dione 21-(dihydrogen phosphate) disodium salt. It comes as a surprise that procaine hydrochloride and dexamethasone sodium phosphate, when used together, can have a positive effect on the treatment of viral diseases. It is known that certain esters like procaine hydrochloride can act synergistically with esters of dexamethasone to prolong procaine hydrochloride anesthetic activity.

Procaine hydrochloride injection is available as a sterile solution in a concentration of 2% (20 mg of procaine hydrochloride in 1 ml solution). Dexamethasone sodium phosphate is available as a sterile solution in a concentration of 0.4% (4 mg of dexamethasone sodium phosphate in 1 ml solution).

The present invention includes a formulation comprising a mixture of procaine hydrochloride and dexamethasone sodium phosphate which is injected intramuscularly at certain dosages and regulated dosing intervals depending on the disease type, patient's severity of condition, age, body build and response to treatment. The following dosage schedule provides an indication of average doses and dosing intervals for adults and children:

For AIDS, Dengue fever and influenza treatment, adult patients can receive an intramuscular injection of around 30 mg of procaine hydrochloride in 1.5 ml of a 20 mg/ml solution mixed with around 2 mg of dexamethasone sodium phosphate in 0.5 ml of a 4 mg/ml solution. The total volume of 2 ml comprising the two compound formulation is aseptically transferred into a sterile 2 milliliter syringe. After the ingredients are gently mixed, the formulation containing syringe is ready for injection. In children, the average dosages are reduce to around 15 mg of procaine hydrochloride in 0.75 ml of a 20 mg/ml solution mixed with around 1 mg of dexamethasone sodium phosphate in 0.25 ml of a 4 mg/mi solution. The total volume of 1 ml comprising the two compound formulation is aseptically transferred to a 1 ml sterile syringe and mixed as described above.

One having ordinary skill in the art will readily recognize that the above ratios and concentrations may be varied and the effect or results may be readily gaged without departing from the spirit and scope of the present invention. Depending on a patient's disease type, severity of condition, age, body build and response to treatment, 5 mg to 40 mg of procaine hydrochloride can be mixed with 1 mg to 4 mg of dexamethasone sodium phosphate per intramuscular injection in order to achieve successful treatment. If the administration of procaine hydrochloride and dexamethasone sodium phosphate in tablet form is contemplated, the dosage amounts for each drug would increase since drug absorption into the circulatory system would occur during drug passage through the gastrointestinal tract whereas drug delivery by intramuscular injection allows for direct drug absorption into the circulatory system. In tablet form, the amount of procaine hydrochloride can be present in a range of about 350 mg to 600 mg and the amount of dexamethasone sodium phosphate can be present in a range of about 25 mg to 40 mg depending on a patient's disease type, severity of condition, age, body build and response to treatment.

For patient treatment, in general, dosing intervals are as follows:

For AIDS treatment, one 2 ml compilation for adults or one 1 ml compilation for children can be injected intramuscularly two times a day having an interval of two hours or more between injections. After a series of daily injections for nine to twelve consecutive days, then two injections per day can be given once a week. Subsequent treatment is determined by laboratory tests for the presence of helper T-cell lymphocytes with CD4 receptors that are susceptible to the HIV envelope glycoprotein gp120. A normal CD4 blood concentration is about 700–1000 cells per cubic millimeter of blood. As the CD4 cell count decreases, the risk of opportunistic viral, bacterial, fungal and parasitic infections increase. Patient dosages can be adjusted depending on the CD4 count and the patient response to treatment.

For Dengue fever, the 2 ml compilation for adults or the 1 ml compilation for children can be injected intramuscularly two times a day having an interval of two hours or more for three to five consecutive days.

For influenza, the 2 ml compilation for adults or the 1 ml compilation for children can be injected intramuscularly two times a day having an interval of two hours or more for one to two days.

All three viral treatments must be accompanied by supplemental oral rehydration fluids. For a severely ill patient, the dosage interval time can be reduced to one and one half hour.

The above average doses and dosing intervals describe a manner and method of making and using the invention and sets forth the best mode contemplated by the inventor for carrying out his invention but is not to be construed as limiting. For example, commercially available formulations of procaine hydrochloride and dexamethasone sodium phosphate may be used provided the amounts of these formulations generally follow the guidelines as set forth within this patent specification. The specification of U.S. Pat. No. 5,492,901 is hereby incorporated by reference noting the following differences: The present invention compilation ingredients are similar except epinephrine (as the hydrochloride) 1:50,000 is omitted. Also, in the present invention the compilation is delivered intramuscularly in different dosage amounts and on a different dosage schedule. Further, the present invention compilation has a surprisingly different use. In the present invention, the compilation treats viral diseases whereas in U.S. Pat. No. 5,492,901 the compilation treats venomous toxin diseases.

Medical Experimentation and Application

Below are documented cases of compassionate experimental treatments from the Fabunan Medical Clinic in Burgos, San Marcelino, Zambales C-2207 Philippines. All experimental administration of the present invention compilation resulted in a compassionate and successful treatment and/or cure. All clinical case studies had patient consent forms signed at the time of treatment. Below are documented accounts of the experimental administration and not a commercial offering of the aforementioned treatment.

Case Number 1; Dengue Fever

E. S., a 55 year old female from Nagbunga, San Marcelino Zambales, Philippines, consulted and treated by the Fabunan Medical Clinic on Aug. 15, 1996 as an outpatient. She had the following complaints; fever of three days duration, maculopapular rash on her chest, lack of appetite and frequent bouts of vomiting. A tourniquet test was positive for Dengue fever and laboratory testing showed a decreased platelet count. She was treated with intramuscular injections containing 30 mg procaine hydrochloride (1.5 ml of a 20 mg per ml solution) combined with 2 mg of dexamethasone sodium phosphate (0.5 ml of a 4 mg per ml solution) (Denguevir-Fabunan Injection, adult dosage) to make a total volume of 2 ml of injectable solution administered twice daily at a two hour interval and coupled with oral rehydration solution. The above symptoms gradually disappeared during a five day course of treatment and the patient fully recovered and was discharged from the clinic.

Case Number 2; Dengue Fever

K. P., nine months old, a female, infant child, from San Marcelino, Zambales, Philippines was accompanied by her mother for consultation at the Fabunan Medical Clinic on Sep. 22, 1996 due to intermittent fever (T=38° C.), with skin rashes, itchiness, and loss of appetite. Tourniquet test was positive with presence of petechial hemorrhage indicative of dengue fever. The patient was treated with intramuscular injections containing 15 mg procaine hydrochloride (0.75 ml of a 20 mg per ml solution) combined with 1 mg of dexamethasone sodium phosphate (0.25 ml of a 4 mg per ml solution) (Denguevir-Fabunan Injection, child dosage) to make a total volume of 1 ml of injectable solution administered twice daily at more than a two hour interval for three days and coupled with supplemental oral rehydration solution. The patient had an improved appetite, all other signs and symptoms gradually disappeared and on the third day as an outpatient, the patient was discharged from the clinic fully recovered.

Case Number 3; Severe Hemorrhagic Dengue Fever

Per a record at Jose B. Lingad Memorial Hospital (JBLMH). G. D. G., a thirteen year old, male, Jehovah's Witness, residing at San Fernando, Pampanga, Philippines, was admitted to JBLMH at Pampanga on Feb. 17, 1999 due to a history of three day high grade fever, anorexia associated with epistaxis (nose bleeding). Prior to hospitalization, medical consultation was done on an outpatient basis where he was sent home with Cephalexin, an oral antibiotic. Outpatient laboratory platelet count equaled 200 X $10^9$/L. (Normal platelet count is 140–340 X $10^9$/L.) Patient had several bouts of vomiting and loose bowel movements (LBM) so he was eventually admitted to the hospital.

On physical examination, he was weak, slightly sunken eyeballs, dry lips and dry skin with vital signs as follows: Blood pressure, 90/60; Temperature, 37.2° C.; Heart rate, 108 beats/min; Weight, 69 lbs. Tourniquet test was negative.

The patient was managed as a case of Dengue Hemorrhagic fever with moderate dehydration. He was placed on nothing per orem (NPO), a nasogastric tube (NGT) was inserted, intravenous (IV) fluids were given along with Paracetamol as well as Ranitidine as medications. The following are initial laboratory results: Blood Hemoglobin, 134 g/L; hematocrit, 0.44 g/L; clotting time and bleeding time were normal, stool positive for occult blood and Trichuris ova; Urine, 0–2 red blood cells; pus cell, 0–1 hpf. Platelet count on admission was 147 X $10^9$/L showing a drop from the count taken two days prior to hospitalization.

During the patient's twenty four hour stay in the hospital, coffee ground materials were noted coming out from the NGT. LBM and vomiting slowly calmed down. Vital signs were apparently stable except for fluctuating temperature.

On the second hospital day, he had episodes of epistaxis and gum bleeding. He complained of abdominal pain and there was a gastrointestinal bleeding as seen with a continuous flow of coffee ground materials from the NGT. A dropping blood pressure, 80/40 was noted. There was a drop of hemoglobin (119 g/L) and his hematocrit was 0.39 g/L. Another IV line was started and Dopamine was hooked to elevate or stabilize his blood pressure. The patient, due to religious belief as a Jehovah's Witness rejected blood transfusions.

On the third hospital day, his blood pressure was 90/60 while his serial platelet count was 100 X $10^9$/L. The patient's condition was going downhill and the doctors evaluated his status as a poor prognosis.

On Feb. 21, 1999, the patient's parent requested that the hospital discharge the patient against hospital advice and the parent sought assistance from the Fabunan Medical Clinic (FMC) in Zambales, Philippines. The patient was brought to FMC by his parent through a private van. He was non-ambulatory, dehydrated, very weak, apprehensive with two IV lines, one with Dopamine drip and the other NGT. His vital signs were as follows: Blood pressure, between 100/60 and 90/60; Temperature, 37.2° C.; pulse rate, 64/min; Weight 66 lbs. Petechial hemorrhages were seen all over his body along with skin flashing. The patient was given two adult doses of Denguevir-Fabunan Injection, 2 cc by intramuscular route at an hour and a half interval. At that time, the patient voided twice. Three hours after the first injection, the patient was seated and was given solid food and sipped some oral fluid solution. NGT was closed. five hours after the initial Denguevir-Fabunan Injection, all IV fluids were terminated/NGT was removed and the patient was advised to take food as tolerated. For the next forty eight hours, he recovered dramatically with better appetite and minimal symptoms. The parents were very happy after seeing the speedy recovery of their son within three days of Denguevir-Fabunan injection. The patient was discharged from the care of the clinic on Feb. 24, 1999 fully recovered and cured. Ten days after discharge, the patient and his parent came to visit the doctors of FMC just to thank them again for his life.

Case Number 4; Dengue Fever

This is the case of a nine year old boy, J.A.A., from Subic, Zambales, Philippines, who was first admitted at a hospital in Zambales and was diagnosed with Dengue fever. A laboratory revealed a decreasing platelet count. Seeking additional medical advice, his parent sought consultation at the Fabunan Medical Clinic in San Marcelino, Zambales, Philippines on Jul. 16, 1998. On physical examination, the patient weighed fifty pounds, was fairly nourished and appeared fairly developed. He had a fever for five days with a temperature of 38° C. A Tourniquet test was positive with the presence of red tiny spots at the anterior cubital fossa of the right arm. No further laboratory platelet count was done. He had loss of appetite, body malaise and petechial rashes at the chest and back. He complained of itchiness all over his body.

Patient was given the Denguevir Fabunan Injection, a child's dosage, 1 cc by intramuscular route twice a day at a two hour interval for three days with supplemental oral rehydration fluid solution as needed. The above signs and symptoms gradually disappeared after the third day of treatment and he was discharged from the clinic as cured.

Case Number 5; Viral Influenza

This is the case of a 66 year old male, S.D.C., married and retired of San Marcelino, Zambales, Philippines, who came for a consultation as an outpatient at the Fabunan Medical Clinic on May 10, 1999. He presented the following complaints: High grade fever (temperature was 40° C.), chills, body malaise, loss of appetite, severe headaches, redness of both eyes, muscle and joint pains of two days duration. Due to his illness, he lay in bed all day. No medications were taken before treatment and no clinical laboratory work up was done.

There were no other pertinent physical findings. He was diagnosed with viral influenza and was given one adult dose of a Influvir-Fabunan injection containing 30 mg procaine hydrochloride (1.5 ml of a 20 mg per ml solution) combined with 2 mg of dexamethasone sodium phosphate (0.5 ml of a 4 mg per ml solution) to make a total volume of 2 ml of injectable solution administered by intramuscular route followed by another dose after a two hour interval. He was also given an oral rehydration solution as needed. Several minutes later, he perspired profusely and went to the restroom repeatedly. He was sent home and then he came back the following morning for a check up. He had a better appetite, rested well in the evening and felt better without any of the above symptoms. He was eventually discharged fully recovered from the care of the clinic.

Case Number 6; AIDS

E.S.B., a 47 year old female, a clinic receptionist residing in MetroManila, Philippines was diagnosed as HIV positive in February, 1996 at an accredited medical research center. As an HIV case, she was provided with a supply of a triple drug therapy; AZT (six capsules), Hivid (six tablets) and Saquinavir (9 capsules). She took these twenty one capsules and tablets orally three times a day at a specific time. The patient was able to take medication from November, 1997 to November, 1998 and she experienced gastric discomfort, occasional vomiting, loss of appetite, constipation, insomnia, depression and skin discoloration. She also stated that her body resistance had lowered and was hospitalized on Apr. 11, 1999 to Apr. 23, 1999 due to body malaise and productive cough. She was discharged with the following diagnoses: Acute bronchitis, non-specific dermatitis and HIV infection.

As related by the patient, she was an ex-overseas contract worker in Hong Kong for seven years. In 1989, she was diagnosed with severe anemia and received a transfusion of six pints of blood. She was also separated from her Filipino husband since 1985 and had experienced foreign multiple sex partners. After November, 1998, up to the time of consultation in May, 1999, she was not taking any medicine for HIV/AIDS due to lack of funds. She voluntarily submitted herself for treatment after an informed consent at the Fabunan Medical Clinic in San Marcelino, Zambales, Philippines. As a compassionate clinical study of Chimpavir-Fabunan injection containing 30 mg procaine hydrochloride (1.5 ml of a 20 mg per ml solution) combined with 2 mg of dexamethasone sodium phosphate (0.5 ml of a 4 mg per ml solution) to make a total volume of 2 ml of injectable solution administered by intramuscular route, this antiviral drug compilation is based on the current usage of Denguevir-Fabunan injection as an antiviral treatment and/or cure for Dengue fever virus.

On May 9, 1999, the patient presented the following signs and symptoms: Loss of appetite, loss of weight, easy fatigability, dryness and discoloration of the skin, depression, disturbance of sleep, headaches and occasional vomiting. Her vital signs were as follows: Blood pressure, 122/70; Temperature, 37° C.; Heart rate, 76/min. Lab tests at St. Luke's Medical Center, Metro Manila revealed the following: May 7, 1999; Elisa (enzyme linked immunosorbent assay) test: HIV I/HIV II reactive. May 8, 1999; Immunodeficiency panel using Coulter flow cytometer: CD3=898; CD4=287; CD8=525. Her weight was 118 lbs.

The patient was administered with the Chimpavir-Fabunan injection; 2 cc by intramuscular twice daily at a two hour interval for nine days ending on May 17, 1999. Day by day, the patient noticed no side effects and she felt better in her daily injections. She stated that all her signs and symptoms were gone. She had an improved appetite, did not complain of fatigue, and was well rested. She no longer had headaches, vomited or suffered from depression. She had good skin turgor, gained weight and now appears in high spirits. On May 18, 1999, her test results were as follows: Elisa test HIV I/HIV II reactive. Repeat immunodeficiency panel at St. Luke's Medical Center: CD3=1217; CD4=405; CD8=709. Her weight was 121 lbs.

In June, 1999, patient was given Chimpavir-Fabunan injection every week, twice daily at a two hour interval with no apparent complaints. At the end of June, a repeat immunodeficiency panel was done at St. Luke's Medical Center: Jun. 29, 1999; CD3=1184; CD4=407; CD8=711. Her weight was 127 lbs.

In July, 1999, patient was given the Chimpavir-Fabunan injection every ten days, twice daily at a two hour interval with no apparent complaints. At the end of July, a repeat immunodeficiency panel was done at St. Luke's Medical Center: Jul. 30, 1999; CD3=1601; CD4=559; CD8=1019. Her weight was 128 lbs.

A maintenance dose of Chimpavir-Fabunan injection is given every ten days, twice daily at a two hour interval, then repeat CD4 count every end of the month. Dosage may be adjusted depending on the CD4 count and patient response to treatment.

It should be noted that the names Chimpavir-Fabunan Injection, Denguevir-Fabunan Injection and Influvir-Fabunan Injection represent trademarks for the compilations of the present invention. The procaine hydrochloride can range from 5 mg to 40 mg per injection and the dexamethasone sodium phosphate can range from 1 mg to 4 mg per injection.

Chimpavir-Fabunan Injection is an alternative treatment for HIV/AIDS. It may not kill the human immunodeficiency virus (HIV) but may slow down the development of AIDS and other opportunistic or life threatening infections. It may restore CD4, CD8 and CD3 lymphocytes' number and function, therefore prolonging and improving the quality of a patient's life.

It will be understood by those skilled in the art that the present invention is not limited to the sole embodiment described above, but encompasses any and all embodiments within the scope of the following claims:

I claim:

1. A method of treatment for human virus diseases in individuals infected with Dengue fever virus or influenza virus comprising administering to said individuals a liquid mixture of procaine hydrochloride and dexamethasone sodium phosphate.

2. The method according to claim 1 wherein said liquid mixture of procaine hydrochloride and dexamethasone sodium phosphate is injected intranmuscularly.

3. The method according to claim 2 wherein said liquid mixture of procaine hydrochloride and dexamethasone sodium phosphatic is present in a range of 5 mg to 40 mg of procaine hydrochloride and a range of 1 mg to 4 mg of dexamethasone sodium phosphate per intramuscular injection, said amount of drug mixture administered depending on the disease type, patient's severity of conditions age, body build and response to treatment.

4. The method of claim 3 wherein said liquid mixture of procaine hydrochloride and dexamethasone sodium phosphate is injected intramuscularly at least twice a day at approximately a one and a half hour or more interval.

5. A method of treatment to alleviate symptoms in individuals infected with human immunodeficiency virus (HIV) comprising administering to said individuals a liquid mixture of procaine hydrochloride and desamethasone sodium phosphate.

6. The method according to claim 5 wherein said liquid mixture of procaine hydrochloride and desamethasone sodium phosphate is injected intramuscularly.

7. The method acccording to claim 6 wherein said liquid mixture of procaine hydrochloride and dexamethasone sodium phosphate is present in a range of 5 mg to 40 mg of procaine hydrochloride and a range of 1 mg to 4 mg of dexamethasone sodium phosphate perintramuscular injection, said amount of drug mixture administered depending on the disease type, patient's severity of condition age body build and response to treatment.

8. The method of claim 7 wherein said liquid mixture of procaine hydrochloride and desamethasone sodium phosphate is injected intramuscularly at least twice a day at approximately a one and a half hour or more interval.

* * * * *